United States Patent [19]

Ivancsics

[11] 4,356,734
[45] Nov. 2, 1982

[54] SOIL SAMPLING DEVICE

[75] Inventor: József Ivancsics, Szekszard, Hungary

[73] Assignee: Dalmándi Állami Gazdaság, Dalmánd, Hungary

[21] Appl. No.: 55,335

[22] Filed: Jul. 6, 1979

[51] Int. Cl.³ .............................................. G01N 1/08
[52] U.S. Cl. .............................. 73/864.31; 73/864.41; 172/438
[58] Field of Search ........... 73/864.41, 864.44, 864.45, 73/864.31, 864.32; 172/19–22, 61–69, 438, 574, 576

[56] References Cited

U.S. PATENT DOCUMENTS 3,264,877 8/1966 Boxrud .............................. 73/864.45
3,464,504 9/1969 Stange .............................. 73/864.45
3,625,296 12/1981 Mahry .............................. 73/864.31
4,252,018 2/1981 Neises .............................. 73/864.32

Primary Examiner—S. Clement Swisher
Attorney, Agent, or Firm—Gabriel P. Katona

[57] ABSTRACT

There is disclosed a soil sampling device having a sampling unit arranged on a disc which can be rotated around a quasi-horizontal axle on the arm of a frame attached to a vehicle. Also on the arm is a sample removing unit which removes the sample from the sampling unit and places it in a sample collection box. The invention provides a means to carry out soil sampling quickly, reproducibly and automatically and obtain an authentic picture of the properties of the investigated soil.

6 Claims, 3 Drawing Figures

SOIL SAMPLING DEVICE

The invention relates to a soil sampling device. As is known, soil sampling devices are used to take so-called "partial samples" from soils to be tested. The "partial-samples" are collected together, whereafter they form the so-called "average sample." The collected "average samples" are subjected to laboratory tests in the course of which the properties of the tested soil, such as the supply of soil nutrients, soil conditions etc. are determined. The investigation of soil based on "average samples" can however only give a true picture of the soil investigated if the "average sample" consists of many "partial samples." Moreover it is an important criterion that the sampling should be carried out quickly and in a reproducible manner. The result of the soil test can decisively influence e.g. the selection of the species of plant to be cultivated in a given area, or the supply of nutrients to the soil, i.e. the the general management.

The soil sampling devices used for the above purpose are, generally, rods or pipes thrust into the soil to be tested to a depth of approximately 20 cm. and then pulled out. During the thrusting into the soil the "partial sample" passes into a recess of the rods or pipes, which recess is developed as a sampling unit. After pulling out the rods or pipes from the soil, the "partial samples" are removed from the sampling unit by scraping out or knocking out and are collected. The thrusting into and pulling out from the soil of the known sampling devices is carried out manually. Such a method is described e.g. by S.L. Tisdale and W.L. Nelson in their work "Soil fertility and fertilisation" (Mezőgazdásagi Kiadó, Budapest, 1966 page 330). Another known method is where the thrust pipe is mounted on a tractor, and the thrusting of pipe into, and pulling out from the soil is performed by a hydraulic cylinder.

In both the manual and the mechanical methods the sampling is discontinuous and slow, requires a large number of operators and contains many sources of subjective errors. A further drawback of the mechanised method is that it is cumbersome to maneuver the tractor exactly to the locations of sampling. These characteristics result in obtaining "average samples" from a relatively small number of "partial samples". Also, another problem with the known methods is that they take time and generally only a limited time period, about 1–2 weeks, is available for sampling, e.g. in the case of corn fields, the time between harvesting and fertilizing or manuring is between 1 and 2 weeks. As a practical matter, the known methods do not permit sufficient sampling in such a short time to provide a reliable picture of the quality and condition of the soil. However, experienced farmers can use the information gained by such methods. Also, sampling is difficult because of plant stubble and roots.

An object of the invention is to eliminate the drawbacks described above.

Accordingly, another object of the invention is to provide a soil sampling device by means of which the sampling can be performed relatively quickly, reproducibly and automatically.

A further object of the invention is to provide a device for continuous sampling having rotating components.

This invention overcomes the above problems by providing a soil sampling device comprising a sampling unit fastened to a disc which rotates around a quasihorizontal shaft. The unit contains a sample removing device which acts in cooperative relationship with the sampling unit.

With the aid of this construction a relatively quick, reproducible and at the same time automatic sampling can be achieved by simple means.

In a preferred embodiment of the invention the sample removing unit is associated with a sample collecting unit in which a predetermined number of samples can be collected.

A particularly simple embodiment is made possible if the sampling unit is constructed as a liftout plate provided with a cutting edge and forming an acute angle with the lateral face of the disc. Here the sample removing unit is a wedge-shaped element protruding at one part of the path of motion of the lift-out plate, between the lateral face of the disc and the lift-out plate and is fastened to an arm supporting the disc.

In a particularly advantageous embodiment of the invention the soil sampling device is provided with a frame that can be coupled to a liftable and lowerable suspension frame of a tractor, on which frame at least one disc is suspended in a self-centering fashion. Here the relative position of the frame and disc can be adjusted.

Finally, it is advantageous if the sample collecting unit consists of a damping element fastened to the arm and a sample collecting box that can be placed into and removed from this element.

The invention is described in greater detail by reference to the drawings showing two exemplary preferred embodiments of the soil sampling device according to the invention. In the drawing.

Figure 1:
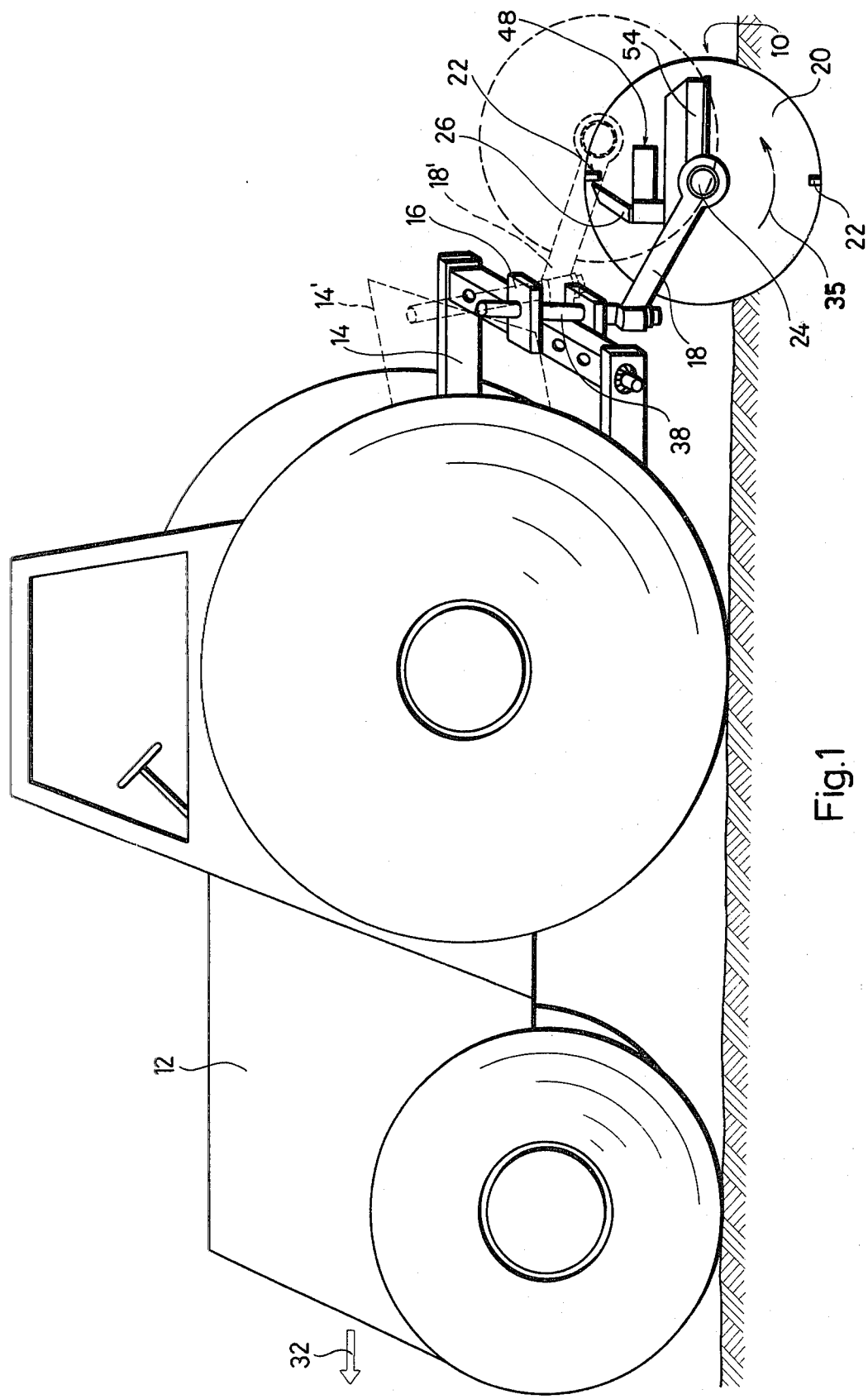
FIG. 1 shows the first preferred embodiment of the sampling device according to the invention, mounted on a tractor, in side view.

As can be seen in FIG. 1, the soil sampling device 10 according to the invention has a frame 16 which in this case can be coupled to the per se known suspension frame 14 of a tractor 12. A disc 20 is suspended on the frame 16 via an arm 18 in a self-aligning fashion i.e. the disc 20 is so arranged that it can be tilted in horiozontal plane. The working position of the disc 20 is indicated by a continuous line while its raised position is indicated by a broken line.

According to the invention, a sampling unit 22 is fixed on the disc 20. In the illustrated case, the disc 20 is pivotally journalled on an arm 18 so as to be rotatable around a horizontal shaft 24. In FIG. 1, the disc 20 is provided with two sampling units 22, but the number of sampling units 22 and their arrangement on the disc 20 can be chosen as desired. The direction of advance of the tractor 12 is indicated by the reference number 32.

According to the invention, the soil sampling device 10 has a sample removing unit 26 which works together with the sampling units 22. The function of unit 26 is to remove the sample lifted from the soil by the sampling unit 22 from the latter.

Figure 2:
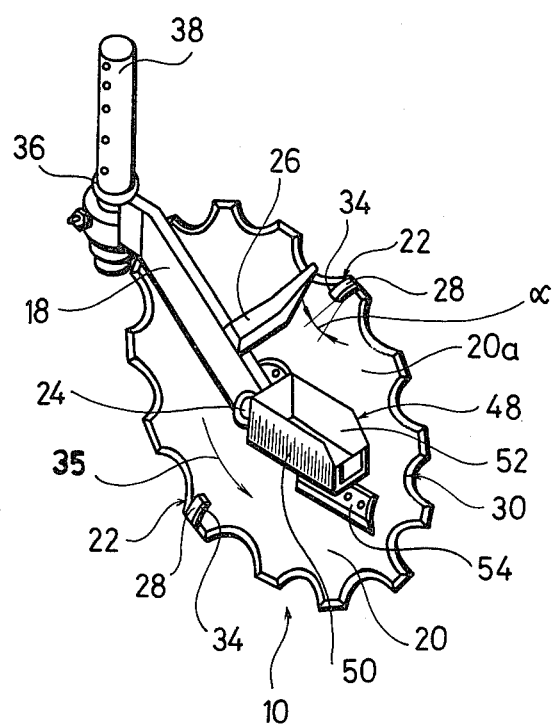
FIG. 2 is a perspective view of a detail of the embodiment of the sampling device according to FIG. 1.

FIG. 2 shows that the sampling unit 22 is constructed as a lift-out plate 28 which forms an acute angle $\alpha$ with the lateral face of the disc 20. In this case the lift-out plate 28 is directly secured by welding to the edge 30 of the disc 20. It is expedient to choose the angle $\alpha$ to be 15°–40°. In this particular case $\alpha = 35°$. The lift out plate 28 is provided with a lateral cutting edge 34. In this embodiment the sample removing unit 26 is a wedge-shaped element which at a portion of the path of the rotary movement of the sampling unit 22 projects between the lift-out plate 28 and the lateral face 20a of the disc 20 and is here secured to the arm 18 by welding. The sense of rotation of the disc 20 is indicated in the drawing by reference number 35.

Figure 3:
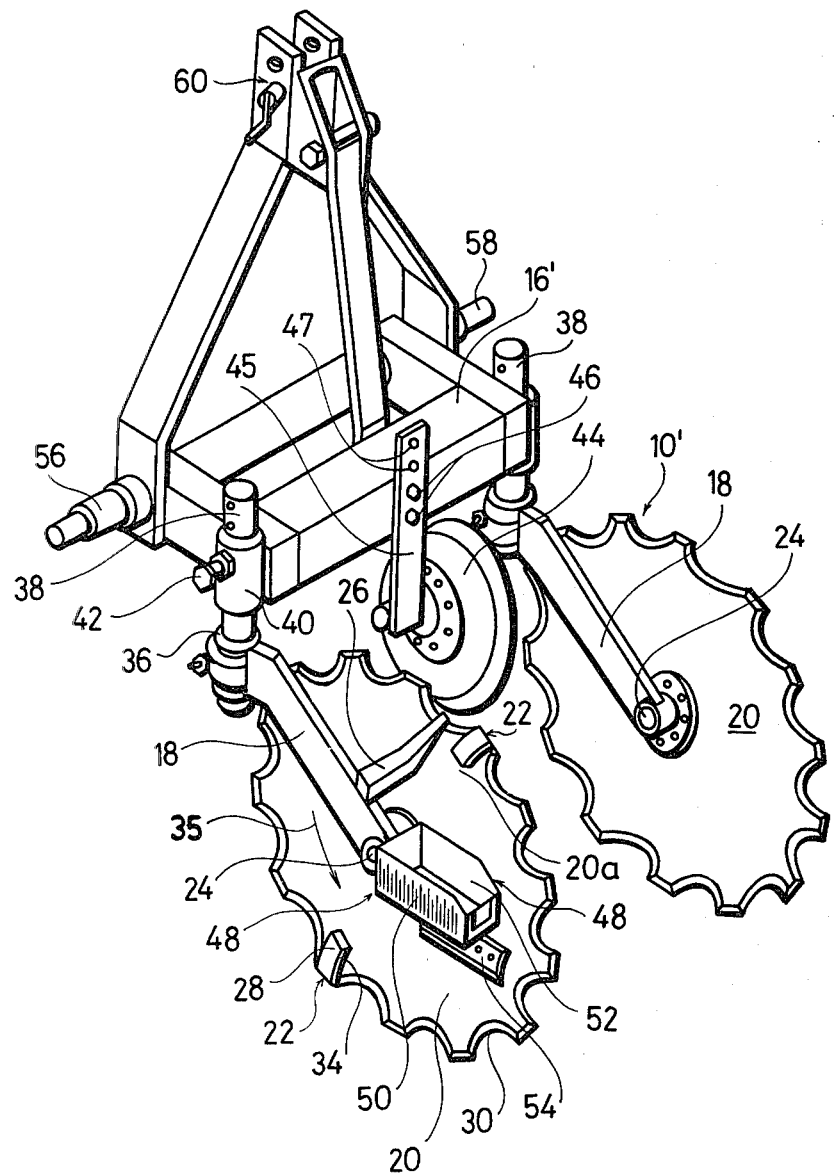
FIG. 3 shows the second preferred embodiment of the soil sampling device according to the invention.

In FIGS. 2 and 3, the disc 20 has been shown as a serrated disc but it can be any other kind of disc. Also, the sampling units 22 do not necessarily need to be secured to the edge 30 of the disc 20, either. Any required number of these units 22 can be arranged at any place on the lateral face 20a of the disc 20, depending on what are the requirements regarding the depth of sampling and the number of samples to be taken from the soil.

In FIG. 3, an embodiment of the soil sampling device 10' is shown wherein two self-aligning discs 20 are arranged in a spaced-apart, side-by-side, manner on the frame 16'. The constructional arrangement of these discs 20 is otherwise identical with the design illustrated in FIGS. 1 and 2. As can be clearly seen in FIG. 3, the arms 18 are coupled to a spigot 38 via e.g. a bronze bush journal 36. The spigot 38 is adjustably fixed in the sleeve 40 of the frame 16' with the aid of a screw 42. The relative height of the frame 16' and the disc 20 is thereby adjustable. An auxiliary wheel 44 may serve for the accurate determination of the working depth of the soil sampling device 10. The relative height of the auxiliary wheel 44 and the height of the frame 16' can be adjusted by screws 46 interchanging the bores 47 in the suspension arm 45 of the auxiliary wheel 44. As is shown in the drawing, in this embodiment the sampling units 22 and the sample removing units 26 are arranged in a mirror symmetry, therefore these details are not visible in FIG. 3 on the righthand disc 20.

According to the invention the sample removing unit 26 is combined with a sample collecting unit 48. In the embodiment illustrated in FIG. 3, the sample collecting unit 48 consists of a U-shaped clamping plate 50 made of steel and fixed to the arm 18, and of a sample collecting box 52 which can be placed into and taken out from the clamping plate 50.

In order to clean the surface 20a of the disc 20 fitted with the sampling unit 22 from bits of soil and impurities adhering thereto, each disc 20 is provided with a cleaning plate 54 made of hard rubber plate and closely fitted to the surface 20a of the disc 20.

The frame 16' shown in FIG. 3 can be coupled in a known manner at suspension points 56, 58 and 60 to the suspension frame 14 of the tractor 12.

The embodiments of the soil sampling device according to the invention and illustrated by way of example operate as follows:

The soil sampling device 10 is transported to the area designated for sampling in its raised position indicated by broken lines in FIG. 1. To this end the tractor driver raises the suspension frame 14 of the tractor 12 by means of an hydraulic cylinder (not shown) into the upper end position for transportation. When the tractor arrives to the field designated for soil sampling, the tractor driver lowers the suspension frame 14, and thus the soil sampling device 10 mounted on the frame 14, into the working position as indicated by unbroken lines in FIG. 1. In the working position the soil sampling device 10 sinks by means of e.g. the auxiliary wheel 44 into the soil to be tested, to a predetermined depth. For practical purposes it is expedient to advance the tractor transversally to the direction of cultivation or tilling. In the course of our experiments the tractor was advanced diagonally on the field. During the advance of the tractor 12 the towed disc 20 performs a forced rotary motion and sinks into the soil to a depth set by the height of the suspension frame 14 or by the auxiliary wheel 44. During the advance of the tractor the sampling units 22 arranged on the disc 20 penetrate into the soil and then emerge from it. With the aid of its cutting edge 34 the lift-out plate 28 progresses easily in the soil and chops any plant remnants it may encounter in its path. At the beginning of the penetration of the sampling unit 22 into the soil the parts of the soil pass between the lift-out plate 28 and the lateral face 20a of the disc 20. However, when the sampling unit 22 reaches the lowermost point of its circular path, it entrains the sample of the soil part trapped at this depth by the lift-out plate 28 and the lateral face 20a of the disc 20 and brings it to the surface through the gap of the soil opened by it. Thus during this time the disc 20 turns in the direction of arrow 35. When the sampling unit 22 reaches the vicinity of the sample removing unit 26, the sample removing unit 26 removes the "part sample" which drops into the box 52 of the sample collecting unit 48. This box 52 is arranged in the region situated below the meeting point of the sampling unit 22 and the sample removing unit 26.

The experience we have gained during testing the described and illustrated embodiments of the soil sampling device according to the invention indicate that it is convenient to take the soil samples from a depth of 15–29 cm.

The volume of box 52 has been selected in such a way that it should be an integral multiple of the volume of the "part sample" of the sampling unit 22. The volume of box 52 should be suitable to accommodate the "average sample". After the box 52 has been filled up it is replaced by an empty box 52, while the filled boxes 52 can be collected in containers not shown in the drawing.

By means of the embodiment illustrated in FIG. 3, parallel samplings can be carried out. Thus double "part samples" can be obtained. In this way the efficiency of sampling may be further improved. In the course of the tests we carried out with the soil sampling device according to the invention, a single tractor driver performed—depending on the conditions of the soil—the sampling of an area of 3–500 hectares in an 8 hour working day.

The main advantages of the solution according to the invention are that the sampling is quick, continuous, reproducible, automatic and the possibility of subjective errors can be eliminated. The "average sample" can be obtained from any discretionally chosen number of "part samples" and from any desired depth of soil. This can be determined by the number and diameter of the discs 20, the number of sampling units 22 and by their arrangement on the discs. With such sampling always an authentic picture of the soil under test is obtained. The handling personnel is limited to the tractor driver and a worker changing the boxes 52. The task of the expert directing the sampling is reduced to giving instructions and the observation of the soil investigated. In the course of our trials, a soil sampling device with one disc took 6 average samples per hectare, while one with two discs took 12 such samples.

With the aid of the proposed sampling device the sampling of large cultivable lands can be carried out in a short time reliably and automatically, thus the efficiency of farming can be substantially increased.

Although in the described embodiments towed discs 20 have been described, according to the invention a embodiment is also possible wherein the discs are provided with separate drives. However, the method of rotating the discs does not form part of the essence of the invention and is not, therefore, described in detail.

I claim:

1. A soil sampling device adapted for attachment to a vehicle comprising:
   (a) at least one substantially vertical disc rotatably connected to a quasi-horizontal axle, said axle being operatively attached perpendicular to an arm connected to a frame for attachment to said vehicle;
   (b) a sampling unit attached to said disc; and
   (c) a sample removing unit attached to said arm in cooperative relationship with said sampling unit.

2. The sampling device according to claim 1 wherein a sample collecting unit is attached to said arm for receiving said sample from said sample removing unit.

3. The sampling device according to claim 1 wherein said sampling unit is a lift out plate having a cutting edge and forming an acute angle with the lateral face of said disc.

4. The sampling device according to claim 3 wherein said sample removing unit is a wedge-shaped element protruding from said arm to said disc into the path of movement of said lift out plate between the lateral face of said disc and said lift out plate.

5. The sampling device according to claim 4 wherein said sample collecting unit comprises a removable collecting box in a clamping element attached to said arm.

6. The sampling device according to claims 1, 2, 3, 4 or 5 wherein said frame is coupled to an adjustable suspension frame of a tractor for adjusting the height of said disc which is suspended on said arm, in a horizontal plane.

* * * * *